(12) United States Patent
Ayoub

(10) Patent No.: US 7,378,549 B2
(45) Date of Patent: May 27, 2008

(54) PROCESS FOR THE REACTIVE EXTRACTIVE EXTRACTION OF LEVULINIC ACID

(75) Inventor: Paul Marie Ayoub, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 11/041,324

(22) Filed: Jan. 24, 2005

(65) Prior Publication Data
US 2006/0047139 A1    Mar. 2, 2006

(30) Foreign Application Priority Data
Jan. 26, 2004    (EP) ................................ 04100272

(51) Int. Cl.
*C07C 59/00* (2006.01)
*C07C 69/66* (2006.01)

(52) U.S. Cl. ...................................... 562/577; 560/174

(58) Field of Classification Search ..................... None
See application file for complete search history.

(56) References Cited

U.S. PATENT DOCUMENTS

| | | | |
|---|---|---|---|
| 2,029,412 A | 2/1936 | Cox et al. | 260/106 |
| 4,442,303 A * | 4/1984 | Mims | 560/191 |
| 4,476,025 A | 10/1984 | Chum et al. | 210/638 |
| 5,562,777 A | 10/1996 | Farone et al. | 127/37 |
| 5,892,107 A | 4/1999 | Farone et al. | 562/515 |
| 6,054,611 A | 4/2000 | Farone et al. | 562/515 |
| 2006/0201879 A1 | 9/2006 | Den Boestert et al. | 210/634 |

FOREIGN PATENT DOCUMENTS

| | | |
|---|---|---|
| EP | 1304320 A2 | 4/2003 |
| EP | 1304320 A3 | 8/2003 |
| GB | 1282926 | 7/1972 |
| WO | 89/10362 | 11/1989 |
| WO | 96/40609 | 12/1996 |
| WO | 97/47579 | 12/1997 |
| WO | 98/19986 | 5/1998 |
| WO | 03/085071 | 10/2003 |

OTHER PUBLICATIONS

PCT International Search Report, International Application No. PCT/EP2005/050316, filed Jan. 26, 2005.
PCT Written Opinion of the International Searching Authority, International Application No. PCT/EP2005/050316, filed Jan. 26, 2005.
H. Kropf: "Houben-Weyl, Methoden der organischen chemie, Teil 1, Band 6/1a" 1980, G. Thieme Verlag, Stuttgart, XP002286016 p. 2, see entry 2-Methyl-propanol and p. 4, see entries of diols.
European Patent Office Communication dated Jul. 12, 2004 including European Search Report dated Jun. 25, 2004 for application No. EP 04100272.

* cited by examiner

*Primary Examiner*—Paul A Zucker

(57) ABSTRACT

A process for the reactive extraction of levulinic acid from an aqueous mixture having levulinic acid, wherein the aqueous mixture is contacted with a liquid esterifying alcohol, the alcohol having at least four carbon atoms and is substantially water-immiscible, at esterification conditions in the presence of a catalyst to form a levulinate ester, wherein the amount of the alcohol is such that the alcohol extracts the levulinate ester from the aqueous mixture. Further, an aqueous phase, having the catalyst and a reduced levulinic acid content, and an organic phase, having the alcohol and the levulinate ester, are formed.

49 Claims, 2 Drawing Sheets

PROCESS FOR THE REACTIVE EXTRACTIVE EXTRACTION OF LEVULINIC ACID

This application claims priority from European Patent Application No. 04100272.6, filed on Jan. 26, 2004, which is hereby incorporated by reference.

FIELD OF THE INVENTION

The present invention relates to a process for the reactive extraction of levulinic acid from an aqueous mixture comprising levulinic acid.

BACKGROUND OF THE INVENTION

Levulinate esters are known to be useful as plasticisers and solvents and have been suggested as fuel additives. Levulinic acid can be obtained by acid hydrolysis of cellulose-containing biomass or sugars derived therefrom. Such acid hydrolysis processes are known in the art, for example from WO 89/10362, WO 96/40609, U.S. Pat. No. 5,892,107 and U.S. Pat. No. 6,054,611. Such acid hydrolysis processes yield an aqueous mixture comprising levulinic acid, formic acid, furfural (if $C_5$-sugars containing hemicelluloses were present in the starting material), and the mineral acid that was used as catalyst for the hydrolysis. In the art, several processes for the preparation of levulinate esters starting from such aqueous mixture obtained by acid hydrolysis of biomass are described.

In U.S. Pat. No. 2,029,412 is disclosed the preparation of 2-methylbutyllevulinate ester by esterifying a concentrated, levulinic acid containing syrup obtained from acid hydrolysis of cane sugar with 2-methylbutanol. Water is removed during the esterification process. After the esterification process has been stopped, alcohol is distilled off. The ester is recovered by vacuum distilling the remaining mixture. In the process of U.S. Pat. No. 2,029,412, the amount of water present during the esterification process is very low, since the starting material is a concentrated syrup and water is removed during the esterification process. Disadvantages of the process are that a large amount of energy is needed for water evaporation and that the mineral acid will remain in the product ester stream.

In WO 98/19986 is disclosed the preparation of a levulinate ester by adding methyl or ethyl alcohol to an aqueous levulinic acid/sulphuric acid mixture and refluxing the resulting mixture. The amount of alcohol is in stoichiometric excess to the amount of levulinic acid. It is mentioned that the levulinate ester can be recovered by phase separation after the excess alcohol is distilled off. Separation of the ester from the resulting mixture by means of chromatography is also mentioned.

In WO 97/47579 is disclosed a process for the separation of levulinic acid from a reaction mixture of water-soluble components wherein the levulinic acid is first esterified with an alcohol to produce a water insoluble ester. The ester is then separated from the reaction mixture and subsequently hydrolysed to yield the acid and the alcohol. The alcohol is present in stoichiometric excess to the amount of levulinic acid. The formation and hydrolysis of methyl levulinate is exemplified.

In GB 1,282,926 is disclosed a process wherein an aqueous, levulinic acid-containing solution is contacted with a water-miscible esterifying solvent to form an esterifying mixture. The esterifying mixture is simultaneously contacted with a water-immiscible organic solvent to extract the esters formed. The water-miscible esterifying solvent is preferably a lower alkyl alcohol having one to five carbon atoms and the water-immiscible organic solvent is preferably benzene or chloroform.

In WO 03/085071 is disclosed a process for the preparation of a mixture comprising levulinic acid esters and formic acid esters from biomass, wherein a reaction mixture comprising levulinic acid and formic acid is contacted with an olefin to form an organic phase containing the levulinic acid esters and formic acid esters and an aqueous phase. The olefin is preferably contacted with the reaction mixture in the presence of a water-immiscible hydrocarbon solvent.

The prior art processes of WO 98/19986, WO 97/47579, GB 1,282,926 and WO 03/085071 have several disadvantages. In the processes such as disclosed in WO 98/19986 and WO 97/47579, an aqueous reaction mixture is obtained that contains a relatively high concentration of organic compounds including furfural. As a consequence, the aqueous mixture has to be treated before it could be recycled, since the presence of furfural in the acid reaction mixture may result in the formation of undesired, tar-like by-products. In the processes as disclosed in GB 1,282,926 and WO 03/085071, the esters are extracted from the reaction mixture during or after esterification by means of a water-immiscible solvent. In these processes both an esterifying agent and an extracting solvent are used. This means that both the solvent and the excess of esterifying agent have to be removed from the product streams if the esters are to be obtained in pure form.

SUMMARY OF THE INVENTION

It has now been found that levulinate esters can be prepared and separated from an aqueous mixture containing levulinic acid by a novel reactive extraction process, wherein the aqueous mixture is contacted with a liquid alcohol that serves both as esterifying alcohol and as solvent for the levulinate ester formed.

Accordingly, the present invention relates to a process for the reactive extraction of levulinic acid from an aqueous mixture comprising levulinic acid, wherein the aqueous mixture is contacted with a liquid esterifying alcohol, the alcohol comprises at least four carbon atoms and is substantially water-immiscible, at esterification conditions in the presence of a catalyst to form a levulinate ester, wherein the amount of the alcohol is such that the alcohol extracts the levulinate ester from the aqueous mixture. Further, an aqueous phase, comprising the catalyst and a reduced levulinic acid content, and an organic phase, comprising the alcohol and levulinate ester, are formed.

An advantage of the novel process is that esterification and separation of the ester from the aqueous reaction mixture are combined in a single reactive extraction step without the need for an additional solvent. The water-immiscible alcohol that is already present as esterifying agent also serves as the solvent for the extraction of the levulinate ester.

Another advantage of the novel process is that a great part of the furfural, which is typically present in aqueous mixtures comprising levulinic acid that are obtained from acid hydrolysis of biomass, moves into the organic alcohol phase. As a consequence, the formation of undesired furfural by-products is minimised.

A further advantage is that the reactive extraction process of the invention can be carried out on the aqueous reaction mixture obtained by acid hydrolysis from biomass, without the need to remove the acid catalyst used in the hydrolysis. The same acid catalyst that is used in the acid hydrolysis process for the preparation of levulinic acid can be used in the reactive extraction process of the invention. A still further advantage is that the aqueous phase that is obtained in the reactive extraction process of the invention has a relatively low level of organic compounds. Therefore, the aqueous phase can be recycled to a levulinic acid-forming acid hydrolysis step for re-use of the acid catalyst. Neutralisation of the acid catalyst is thus avoided. If the acid catalyst is sulphuric acid, the formation of gypsum which is formed upon neutralisation of sulphuric acid with lime, is avoided.

DETAILED DESCRIPTION OF THE INVENTION

Figure 1:
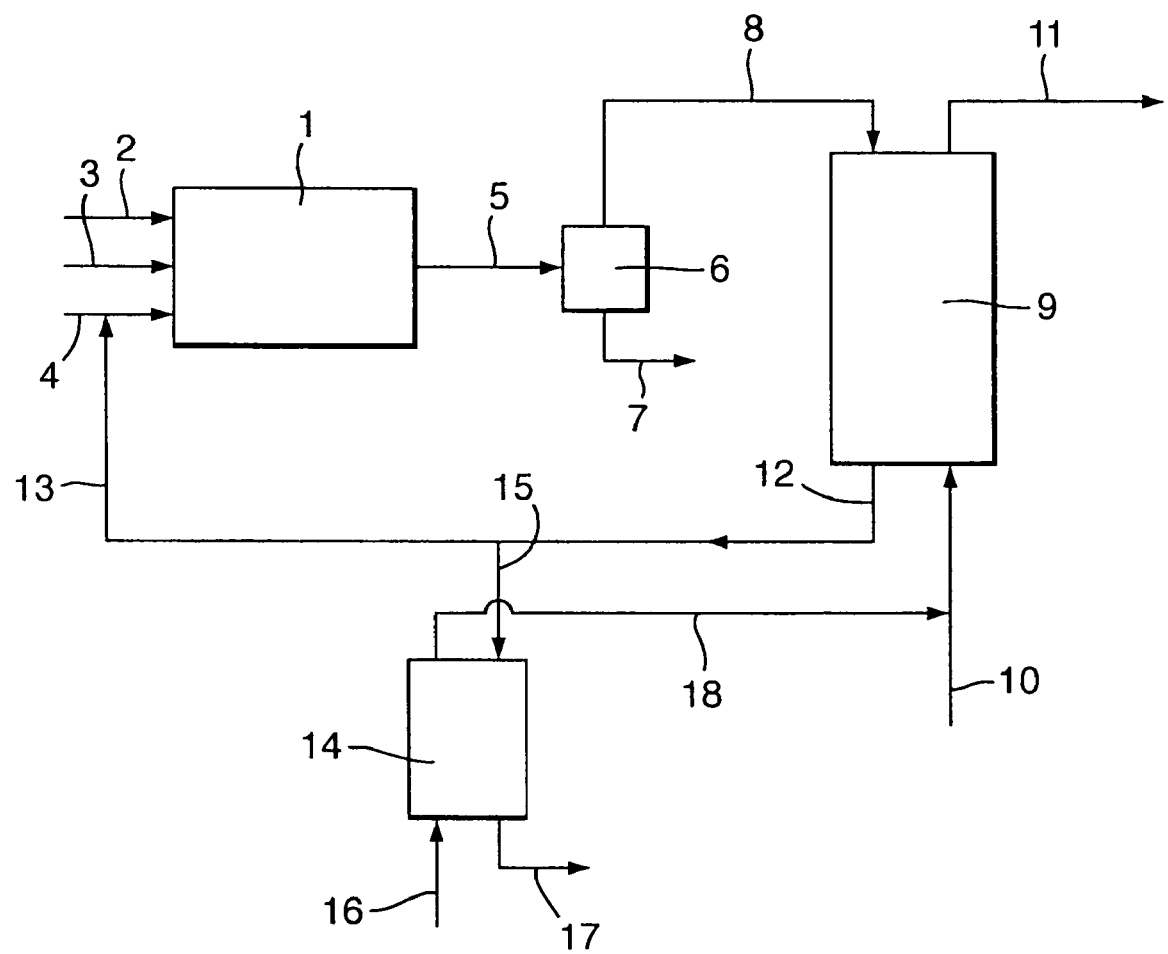
FIG. 1 schematically depicts a flow diagram of an embodiment of the process of the invention comprising an acid hydrolysis step and a reactive extraction step with recycle of the acid catalyst to the hydrolysis step.

In a process according to the present invention, levulinic acid is reactively extracted from an aqueous mixture. The aqueous mixture comprising the levulinic acid is preferably an aqueous mixture as obtained after acid hydrolysis of biomass or of $C_6$ sugars derived from biomass. Reference herein to biomass is to lignocellulosic or cellulosic material comprising cellulose, optionally in combination with hemicellulose or lignin. Acid hydrolysis processes wherein $C_6$ sugars or biomass are converted into levulinic acid and formic acid are known in the art, for example from WO 89/10362, WO 96/40609, U.S. Pat. No. 5,892,107 and U.S. Pat. No. 6,054,611. Furfural is also formed when the starting material contains $C_5$-sugars or hemicelluloses comprising $C_5$-sugars. The hydrolysis is catalysed by an homogeneous acid catalyst, typically sulphuric acid. The hydrolysate is typically separated into a solid fraction comprising lignin residue and unreacted polysaccharides and a liquid fraction. This liquid fraction typically comprises levulinic acid, formic acid, furfural and acid catalyst. This liquid fraction is very suitable as the starting aqueous mixture of the process according to the present invention. No further concentration or separation steps are needed. Typically, the water-to-levulinic acid weight ratio in such liquid fraction is at least 5, usually at least 8.

The aqueous mixture comprising levulinic acid preferably comprises water and levulinic acid in such amounts that the water-to-levulinic acid weight ratio is at least 3.0, more preferably at least 5.0, even more preferably at least 8.0. The water-to-levulinic acid weight ratio is preferably at most 20.

In a process according to the present invention, the aqueous mixture comprising levulinic acid is contacted, at esterification conditions, with a liquid alcohol. The alcohol is an alcohol that is substantially water-immiscible. Reference herein to substantially water-immiscible is to an alcohol that has a solubility in water of less than 15 grams per 100 ml at 20° C. This means that the alcohol has at least four carbon atoms. Certain alcohols with at least four carbon atoms are however miscible with water, e.g. 2-methylpropan-2-ol (tert.-butanol), butane-1,4-diol, butane-2,3-diol, and pentane-1,5-diol. These alcohols are not suitable to be used in a process according to the present invention.

Preferably the alcohol has 5 to 12 carbon atoms, more preferably 5 to 10 carbon atoms. The alcohol is contacted with the aqueous mixture in an amount that exceeds the stoichiometric amount that is needed to esterify the organic acids, i.e. levulinic acid and formic acid, present. The amount of alcohol has to be such that the alcohol can serve as an extracting solvent for the esters formed and that an aqueous phase and an organic phase comprising the alcohol and the esters can thus be formed. This means that the amount of alcohol is such that the alcohol concentration exceeds the solubility of the alcohol in the aqueous phase. Preferably, the amount of alcohol is such that the alcohol/levulinate ester molar ratio in the organic phase is at least 1.0, more preferably at least 1.5, even more preferably at least 2.0. Preferably, the alcohol/levulinate ester molar ratio in the organic phase is at most 50.

The process conditions in the reactive extraction process according to the invention are such that esterification takes place and that the levulinate ester formed is simultaneously extracted from the aqueous phase to the organic alcohol phase. Thus, an aqueous phase having a reduced levulinic acid content as compared to the starting aqueous mixture and an organic phase comprising alcohol and levulinate ester is formed. If furfural is present in the starting aqueous mixture, furfural will be extracted from the aqueous phase to the organic phase.

A catalyst is present to catalyse the esterification reaction. Suitable catalysts for such an esterification reaction are known in the art. The catalyst may be a homogeneous catalyst or a heterogeneous catalyst. Preferably, the catalyst is an acid catalyst, more preferably a mineral acid or a sulphonic acid, for example sulphuric acid, p-toluene sulphonic acid, phosphoric acid, and nitric acid. Sulphuric acid is particularly preferred. The catalyst concentration in the aqueous phase is typically in the range of from 0.5 to 20% by weight, preferably of from 1 to 7% by weight.

In order to allow the esterification reaction to take place, the process temperature will be at least 50° C. In order to allow the extraction to proceed, the organic and the aqueous phase should both be in liquid state. Therefore, the pressure will be at least ambient pressure and the temperature is at most 250° C. It will be appreciated that the higher the process temperature, the higher the process pressure to keep the alcohol and water in liquid state. Preferably, the temperature is in the range of from 60 to 150° C., more preferably of from 80 to 120° C. Preferably, the process pressure is in the range of from 1 to 30 bar (absolute), more preferably of from 1 to 10 bar (absolute), even more preferably of from 1 to 5 bar (absolute).

The alcohol preferably has 5 to 12 carbon atoms. Preferably, the alcohol is a cyclic or non-cyclic alkyl alcohol, for example 1- or 2-pentanol, 1- or 2-hexanol, cyclohexanol, 2-ethylhexan-1-ol, or 1-decanol. A particularly preferred alcohol is 1-pentanol. An advantage of the use of 1-pentanol is that it is obtainable from furfural or from levulinic acid by hydrogenation. It is therefore possible to obtain 1-pentanol by using the furfural that is present in the process of the invention as starting material or by hydrolysing part of the pentyl levulinate obtained and converting the levulinic acid thus-obtained into 1-pentanol.

The reactive extraction process according to the invention may be performed as a batch process or as a continuous process. Preferably, it is performed as a continuous process, wherein the aqueous mixture and the alcohol are countercurrently supplied to an extraction column or to a series of mixer-settlers. More preferably, the process is performed in a countercurrent reactive extraction column. The column may be an empty vessel or may be filled with packing material to enhance the liquid-liquid contact. The packing may be a random packing or a structured packing. The packing material may be inert material or material that is doped with an esterification enhancing catalyst.

Levulinate ester and/or alcohol may be separated from the organic phase by means known in the art, for example by distillation, extraction, reactive distillation, adsorption or combinations thereof. Other compounds that might be present in the organic phase such as furfural and formate ester, may also be separated from the organic phase.

Preferably, at least part of the alcohol separated from the organic phase is recycled to the reactive extraction reactor and thus contacted with the aqueous mixture comprising levulinic acid.

Preferably, the process further comprises an acid hydrolysis step wherein (ligno)cellulosic material, sugars derived therefrom, and combinations thereof are hydrolysed in the presence of a homogeneous acid catalyst to provide the aqueous mixture comprising levulinic acid. The acid hydrolysis step may be any levulinic acid producing acid hydrolysis process known in the art. It may for example be the two-stage process as disclosed in WO 89/10362 and WO 96/40609, or the process as disclosed in U.S. Pat. No. 6,054,611. If the hydrolysate contains solid material, typically lignin residue and unreacted polysaccharides, it is preferred to separate the solid fraction from the liquid fraction by for example filtration or decantation. The thus-obtained liquid fraction is the aqueous mixture.

In such process combining acid hydrolysis and reactive extraction, it is advantageous to use the same acid catalyst in the acid hydrolysis step and in the reactive extraction step. If the same acid is used, at least part of the aqueous phase comprising the acid catalyst, i.e. the aqueous phase formed in the reactive extraction step, is preferably recycled to the acid hydrolysis step.

It might be desirable to purge part of the aqueous phase, i.e. to recycle only part of the aqueous phase to the acid hydrolysis step, to prevent build-up of undesired compounds in the process. In that case, a small part of the aqueous phase is withdrawn from the process. The part to be withdrawn may be extracted, preferably with the same alcohol as used in the reactive extraction step, to extract the remaining organic compounds such as levulinic acid, formic acid, furfural, levulinate ester, formate ester and the like from the aqueous phase. Thus, a second aqueous phase and a second organic, alcohol phase is formed. The second aqueous phase is withdrawn from the process. If the same alcohol as in the reactive extraction step is used, the alcohol extractant (second organic phase) may be added to the alcohol that contacts the aqueous mixture comprising levulinic acid.

If the process according to the invention combines acid hydrolysis and reactive extraction, it might be advantageous to perform the reactive extraction at substantially the same pressure and/or temperature as in the preceding acid hydrolysis. It will be appreciated that if the acid hydrolysis comprises more than one stage, the reactive extraction is preferably performed at the pressure and/or temperature of the last hydrolysis stage.

Figure 2:
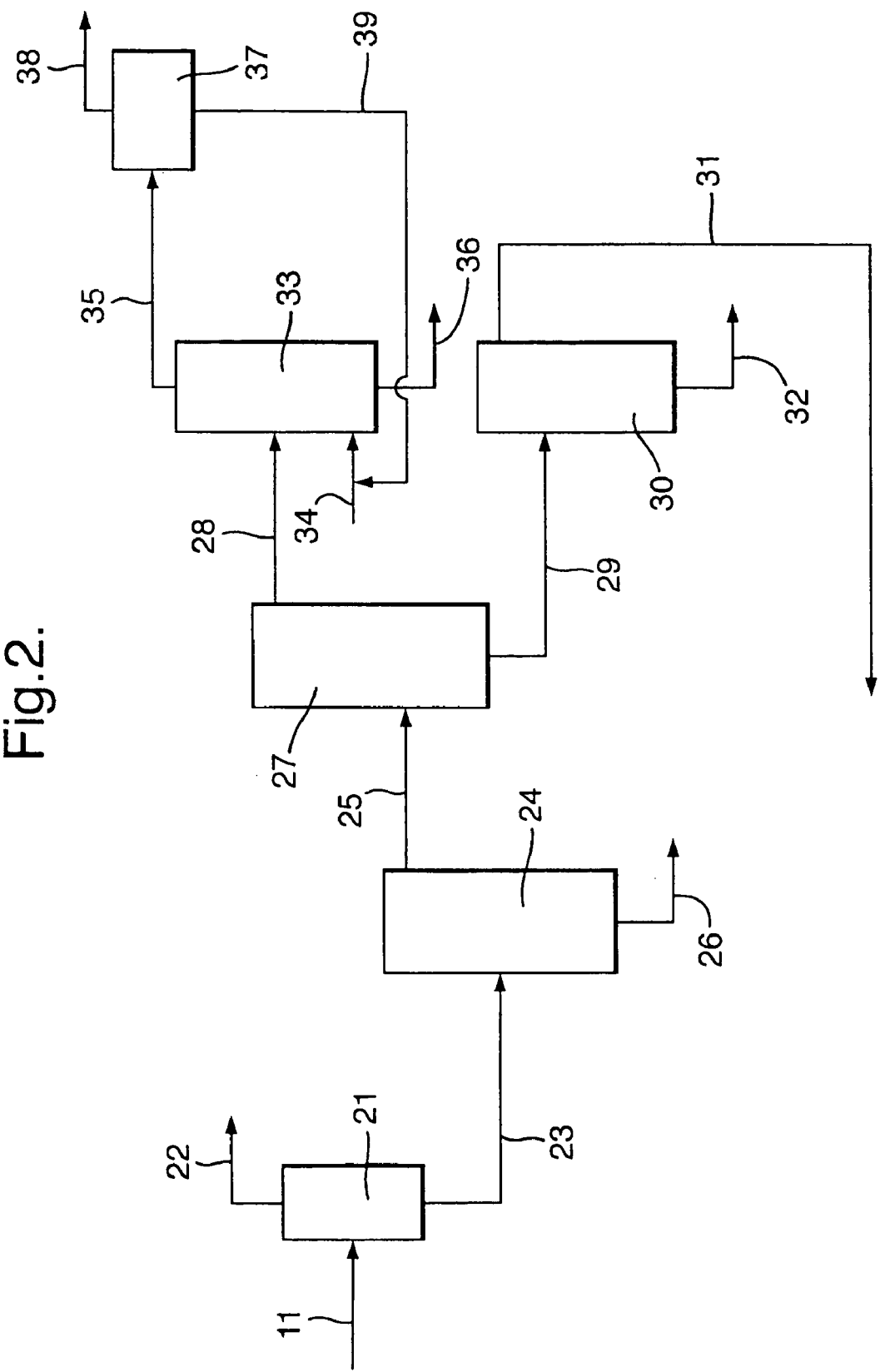
FIG. 2 schematically depicts a flow diagram of a way of separating the levulinate ester and the alcohol from the organic phase.

The invention is further illustrated by way of example with reference to FIGS. 1 and 2.

In FIG. 1 is shown an embodiment of a process of the present invention. Finely divided solid biomass material, sulphuric acid, and water are supplied to acid hydrolysis reaction zone 1 via lines 2, 3 and 4, respectively. The acid hydrolysis reaction zone 1 may comprise more than one acid hydrolysis reactor. A hydrolysate comprising levulinic acid, formic acid, furfural, sulphuric acid, and solid residue is discharged from reaction zone 1 via line 5 and supplied to filtration unit 6. In filtration unit 6, the hydrolysate is separated into a solid fraction 7 and an liquid fraction. Filtration unit 6 may be a simple filter, but it may also further comprise equipment for washing and/or drying.

The liquid fraction comprises levulinic acid, formic acid, furfural, and sulphuric acid. The liquid fraction is supplied via line 8 to reactive extraction reactor 9. 1-pentanol, which may be fresh pentanol and/or recycled pentanol, is counter-currently supplied to reactor 9 via line 10. In reactive extraction reactor 9, levulinic acid and formic acid react with 1-pentanol to form pentyl levulinate and pentyl formate. The esters formed and furfural will be extracted to the organic, pentanol phase. Thus, an aqueous phase comprising sulphuric acid and an organic phase comprising 1-pentanol, pentyl levulinate, pentyl formate and furfural are formed. The organic, pentanol phase is discharged from reactor 9 via line 11 and may be separated into its individual components in a product separation section (see FIG. 2). The aqueous phase is discharged from reactor 9 via line 12 and for the greater part recycled to acid hydrolysis reaction zone 1 via line 13. Part of the aqueous phase is fed to extraction column 14 via line 15. 1-Pentanol is supplied to extraction column 14 via line 16. In column 14, the remainder of the organic compounds is extracted from the aqueous phase to yield a second aqueous phase that is removed from the process via line 17 and a second organic pentanol phase that is recycled to reactive extraction reactor 9 via line 18.

A small part of the aqueous phase may be used for washing the residue obtained after filtration in filter unit 6 and added to line 13 after washing.

In FIG. 2 is shown a process for the separation of pentyl levulinate and pentanol from the organic phase. An organic pentanol phase comprising 1-pentanol, furfural, pentyl-levulinate, pentyl-formate and some water is supplied via line 11 (see also FIG. 1) to drier 21, wherein water is distilled from the organic phase. Water is discharged from drier 21 as overhead stream via line 22 and a dried organic phase is discharged as bottoms stream via line 23 and supplied to distillation unit 24. In distillation unit 24, an overhead stream comprising pentanol, pentyl-formate and furfural is separated from a bottoms stream comprising pentyl-levulinate. The overhead stream and the pentyl-levulinate stream are discharged from unit 24 via lines 25 and 26, respectively. The overheads stream in line 25 is fed to distillation unit 27, wherein it is separated in an azeotropic mixture of pentyl-formate and pentanol and a bottoms stream comprising furfural and pentanol, which streams are discharged from distillation unit 27 via lines 28 and 29 respectively. The stream comprising furfural and pentanol is supplied to distillation unit 30 wherein it is separated into pentanol (overhead stream) and furfural (bottoms stream). The pentanol is discharged via line 31 and recycled to reactive extraction reactor 9 (see FIG. 1) by recombining it with the pentanol stream in line 10 (see FIG. 1). Furfural is discharged from unit 30 via line 32. The mixture of pentyl formate and pentanol in line 28 is supplied to reactive distillation column 33. Water is supplied to column 33 via line 34. In reactive distillation column 33, pentyl formate is hydrolysed into 1-pentanol and formic acid. Pentanol/water is distilled from column 33 as overhead stream and formic acid as bottoms stream. The streams are discharged from column 33 via lines 35 and 36, respectively. The pentanol/water mixture is led to separator 37 and separated into pentanol (discharged via line 38) and water. The water is recycled, via line 39, to reactive distillation column 33.

EXAMPLES

The invention will be further illustrated by means of the following non-limiting examples.

Example 1

In a round bottom flask, 13.5 grams of water, 15.7 grams of 1-pentanol, 1.5 grams of levulinic acid, and 0.8 grams of sulfuric acid were mixed and stirred at 98° C. for 60 minutes. To stop the reaction, the flask was then immersed in an ice batch, while stirring its contents until the mixture reached ambient temperature. The mixture was then allowed to settle, and an aqueous and an organic phase were obtained. The composition of the two phases was analysed and showed that 85% of the levulinic acid was converted into pentyl levulinate, that over 99% of the pentyl levulinate was in the organic phase, and that the molar ratio of pentanol to pentyl levulinate in the organic phase was 15.4.

Example 2

In a round bottom flask, 108.8 grams of water, 125.0 grams of 1-pentanol, 12.5 grams of levulinic acid, and 3.8 grams of sulfuric acid were mixed and stirred at 150° C. for 45 minutes. To stop the reaction, the flask was then immersed in an ice batch, while stirring its contents until the mixture reached ambient temperature. The mixture was then allowed to settle, and an aqueous and an organic phase were obtained. The composition of the two phases was analysed and showed that 67% of the levulinic acid was converted into pentyl levulinate, that over 99% of the pentyl levulinate was in the organic phase, and that the molar ratio of pentanol to pentyl levulinate in the organic phase was 18.5.

Example 3

In a round bottom flask, 36.2 grams of water, 20.1 grams of 1-pentanol, 4.0 grams of levulinic acid, and 2.1 grams of sulfuric acid were mixed and stirred at 59° C. for 30 minutes. To stop the reaction, the flask was then immersed in an ice batch, while stirring its contents until the mixture reached ambient temperature. The mixture was then allowed to settle, and an aqueous and an organic phase were obtained. The composition of the two phases was analysed and showed that 14% of the levulinic acid was converted into pentyl levulinate, that over 95% of the pentyl levulinate was in the organic phase, and that the molar ratio of pentanol to pentyl levulinate in the organic phase was 47.0.

Example 4

The process of the invention as depicted in FIG. 1 is further illustrated by means of process simulation calculations using ASPEN Plus software.

In a process line-up as shown in FIG. 1, once it has reached a steady state, a flow of 83.3 t/h (tons per hour) of hardwood sawdust containing 40% cellulose, 25% hemicelluloses (mainly xylan), 20% lignin, and 15% ash was supplied to acid hydrolysis reaction zone 1 via line 2, together with 0.8 t/h make-up sulphuric acid (line 3) and 8.5 t/h make-up water (line 4) and 512.3 t/h recycled aqueous phase (line 13). In reaction zone 1, the biomass is hydrolysed as described in WO 96/40609, i.e. in a continuous two-stage process wherein the biomass is hydrolysed in a first reactor without significant axial mixing at 220° C. to obtain an intermediate that is supplied to a second reactor with substantial backmixing, wherein the intermediate is further reacted at 210° C.

The resulting hydrolysate (605.0 t/h) is withdrawn from acid hydrolysis reaction zone via line 5 and separated into a solid fraction and a liquid fraction in filtration unit 6. The solid fraction (30.7 t/h) is withdrawn from the process via line 7 and the liquid fraction (574.3 t/h) is supplied to reactive extraction column 9 via line 8. Fresh 1-pentanol (40.0 t/h) and the second organic phase from extraction column 14 (24.5 t/h) are together supplied to the other end of reactive extraction reactor 9 via lines 10 and 18, respectively. In reactive extraction reactor 9, esterification and extraction are carried out at 85° C. and 4 bar (absolute). The resulting organic phase (110.6 t/h) and aqueous phase (528.2 t/h) are withdrawn from extraction reactor 9 via lines 11 and 12, respectively. Part of the aqueous phase (15.8 t/h) is supplied to extraction column 14 via line 15. A stream of 20 t/h of 1-pentanol is supplied to extraction column 14 via line 16. A second aqueous phase and a second organic phase are formed in column 14. The second aqueous phase is withdrawn from the process via line 17 (11.3 t/h) and the second organic phase (24.5 t/h) is via line 18 combined with the fresh pentanol in line 10 and supplied to reactive extraction reactor 9.

The mass flows and the composition of the various liquid streams are shown in the Table below. The conversion of levulinic acid into pentyl levulinate is 70%, and 88% of the pentyl levulinate formed is in the organic phase.

TABLE

Mass flow and composition of the various process streams

| | stream in line no. | | | | | | | | | | | | | |
|---|---|---|---|---|---|---|---|---|---|---|---|---|---|---|
| | 2 | 3 | 4 | 5 | 7 | 8 | 10 | (10 + 18) | 11 | 12 | 13 | 15 | 16 | 17 | 18 |
| mass flow (tons/hr) | 83.3 | 0.8 | 8.5 | 605.0 | 30.7 | 574.3 | 40.0 | 64.5 | 110.6 | 528.2 | 512.3 | 15.8 | 20.0 | 11.3 | 24.5 |
| composition (% by weight) | | | | | | | | | | | | | | | |
| water | | | 100 | | | 66.6 | | 3.8 | 8.7 | 72.1 | 72.1 | 72.1 | | 79.3 | 9.9 |
| furfural | | | | | | 5.1 | | 0.7 | 13.6 | 2.7 | 2.7 | 2.7 | | — | 1.8 |
| sulphuric acid | | 100 | | | | 4.3 | | — | 0.01 | 4.7 | 4.7 | 4.7 | | 6.6 | — |
| levulinic acid | | | | | | 4.8 | | 0.2 | 4.0 | 0.7 | 0.7 | 0.7 | | — | 0.5 |
| formic | | | | | | 8.3 | | 0.7 | 2.0 | 7.5 | 7.5 | 7.5 | | 6.6 | 1.8 |

TABLE-continued

Mass flow and composition of the various process streams stream in line no.

| | 2 | 3 | 4 | 5 | 7 | 8 | 10 | (10 + 18) | 11 | 12 | 13 | 15 | 16 | 17 | 18 |
|---|---|---|---|---|---|---|---|---|---|---|---|---|---|---|---|
| acid | | | | | | | | | | | | | | | |
| 1-pentanol | | | | | | 7.8 | 100 | 93.8 | 29.1 | 8.8 | 8.8 | 8.8 | 100 | 7.5 | 83.8 |
| pentyl formate | | | | | | 2.4 | | 0.7 | 14.4 | 2.7 | 2.7 | 2.7 | | — | 1.7 |
| pentyl levulinate | | | | | | 0.7 | | 0.2 | 28.1 | 0.8 | 0.8 | 0.8 | | — | 0.5 |

What is claimed is:

1. A process for the reactive extraction of levulinic acid from an aqueous mixture comprising levulinic acid, wherein the aqueous mixture is contacted with a liquid esterifying alcohol, the alcohol comprises at least four carbon atoms and is substantially water-immiscible, at esterification conditions in the presence of a catalyst to form a levulinate ester, wherein the amount of the alcohol is such that the alcohol extracts the levulinate ester from the aqueous mixture wherein one liquid esterifying alcohol is utilized.

2. A process according to claim 1, wherein an aqueous phase, comprising the catalyst and a reduced levulinic acid content, and an organic phase, comprising the alcohol and the levulinate ester, are formed.

3. A process according to claim 1, wherein the aqueous mixture comprising levulinic acid comprises water and levulinic acid in such amounts that the water-to-levulinic acid weight ratio is at least 3.0.

4. A process according to claim 1, wherein the aqueous mixture comprising levulinic acid comprises water and levulinic acid in such amounts that the water-to-levulinic acid weight ratio is at least 5.0.

5. A process according to claim 1, wherein the aqueous mixture comprising levulinic acid comprises water and levulinic acid in such amounts that the water-to-levulinic acid weight ratio is at least 8.0.

6. A process according to claim 2, wherein the amount of the alcohol is such that the molar ratio between the alcohol and the levulinate ester in the organic phase is at least 1.0.

7. A process according to claim 2, wherein the amount of the alcohol is such that the molar ratio between the alcohol and the levulinate ester in the organic phase is at least 1.5.

8. A process according to claim 2, wherein the amount of the alcohol is such that the molar ratio between the alcohol and the levulinate ester in the organic phase is at least 2.0.

9. A process according to claim 1, wherein the alcohol comprises 5 to 12 carbon atoms.

10. A process according to claim 9, wherein the alcohol comprises 5 to 10 carbon atoms.

11. A process according to claim 10, wherein the alcohol is 1-pentanol.

12. A process according to claim 1, wherein the catalyst is an acid catalyst.

13. A process according to claim 12, wherein the catalyst is a mineral acid.

14. A process according to claim 13, wherein the catalyst is sulphuric acid.

15. A process according to claim 1, wherein the aqueous mixture is contacted with the alcohol at a temperature in the range of from 50 to 250° C.

16. A process according to claim 15, wherein the aqueous mixture is contacted with the alcohol at a temperature in the range of from 60 to 150° C.

17. A process according to claim 16, wherein the aqueous mixture is contacted with the alcohol at a temperature in the range of from 60 to 150° C.

18. A process according to claim 1, wherein the aqueous mixture is contacted with the alcohol at a pressure in the range of from 1 to 30 bar (absolute).

19. A process according to claim 18, wherein the aqueous mixture is contacted with the alcohol at a pressure in the range of from 1 to 10 bar (absolute).

20. A process according to claim 19, wherein the aqueous mixture is contacted with the alcohol at a pressure in the range of from 1 to 5 bar (absolute).

21. A process according to claim 1, wherein the aqueous mixture comprising levulinic acid is countercurrently contacted with the alcohol.

22. A process according to claim 1, wherein the process is a continuous process.

23. A process according to claim 2, further comprising separating the levulinate ester from the organic phase.

24. A process according to claim 2, further comprising separating the alcohol from the organic phase.

25. A process according to claim 24, wherein at least part of the alcohol separated from the organic phase is contacted with the aqueous mixture comprising levulinic acid.

26. A process according to claim 1, further comprising an acid hydrolysis step, wherein (ligno)cellulosic material, sugars derived therefrom, and combinations thereof are hydrolysed in the presence of a homogeneous acid catalyst to provide the aqueous mixture comprising the levulinic acid.

27. A process according to claim 2, further comprising an acid hydrolysis step, wherein (ligno)cellulosic material, sugars derived therefrom, and combinations thereof are hydrolysed in the presence of a homogeneous acid catalyst to provide the aqueous mixture comprising the levulinic acid, and further wherein at least part of the aqueous phase comprising the catalyst is recycled to the acid hydrolysis step.

28. A process for the reactive extraction of levulinic acid from an aqueous mixture comprising levulinic acid, wherein the aqueous mixture is contacted with a liquid esterifying alcohol, the alcohol comprises at least four carbon atoms and is substantially water-immiscible, at esterification conditions in the presence of a catalyst to form a levulinate ester, wherein the amount of the alcohol is such that the alcohol extracts the levulinate ester from the aqueous mixture, further comprising an acid hydrolysis step, wherein (ligno)cellulosic material, sugars derived therefrom, and combinations thereof are hydrolysed in the presence of a homogeneous acid catalyst to provide the aqueous mixture comprising the levulinic acid wherein one liquid esterifying alcohol is utilized.

29. A process according to claim 28, wherein the aqueous mixture comprising levulinic acid comprises water and levulinic acid in such amounts that the water-to-levulinic acid weight ratio is at least 3.0.

30. A process according to claim 28, wherein the aqueous mixture comprising levulinic acid comprises water and levulinic acid in such amounts that the water-to-levulinic acid weight ratio is at least 5.0.

31. A process according to claim 28, wherein the aqueous mixture comprising levulinic acid comprises water and levulinic acid in such amounts that the water-to-levulinic acid weight ratio is at least 8.0.

32. A process for the reactive extraction of levulinic acid from an aqueous mixture comprising levulinic acid, wherein the aqueous mixture is contacted with a liquid esterifying alcohol, the alcohol comprises at least four carbon atoms and is substantially water-immiscible, at esterification conditions in the presence of a catalyst to form a levulinate ester, wherein the amount of the alcohol is such that the alcohol extracts the levulinate ester from the aqueous mixture, wherein an aqueous phase, comprising the catalyst and a reduced levulinic acid content, and an organic phase, comprising the alcohol and the levulinate ester, are formed, further comprising an acid hydrolysis step, wherein (ligno)cellulosic material, sugars derived therefrom, and combinations thereof are hydrolysed in the presence of a homogeneous acid catalyst to provide the aqueous mixture comprising the levulinic acid, and further wherein at least part of the aqueous phase comprising the catalyst is recycled to the acid hydrolysis step wherein one liquid esterifying alcohol is utilized.

33. A process according to claim 32, wherein the aqueous mixture comprising levulinic acid comprises water and levulinic acid in such amounts that the water-to-levulinic acid weight ratio is at least 3.0.

34. A process according to claim 32, wherein the aqueous mixture comprising levulinic acid comprises water and levulinic acid in such amounts that the water-to-levulinic acid weight ratio is at least 5.0.

35. A process according to claim 32, wherein the aqueous mixture comprising levulinic acid comprises water and levulinic acid in such amounts that the water-to-levulinic acid weight ratio is at least 8.0.

36. A process according to claim 1, wherein the aqueous mixture further comprises formic acid.

37. A process according to claim 36, wherein the aqueous mixture further comprises furfural.

38. A process according to claim 26, wherein no further concentration steps regarding the aqueous mixture are needed after the acid hydrolysis step.

39. A process according to claim 26, wherein no further separation steps regarding the aqueous mixture are needed after the acid hydrolysis step.

40. A process according to claim 27, wherein no further concentration steps regarding the aqueous mixture are needed after the acid hydrolysis step.

41. A process according to claim 27, wherein no further separation steps regarding the aqueous mixture are needed after the acid hydrolysis step.

42. A process according to claim 28, wherein the aqueous mixture further comprises formic acid.

43. A process according to claim 42, wherein the aqueous mixture further comprises furfural.

44. A process according to claim 28, wherein no further concentration steps regarding the aqueous mixture are needed after the acid hydrolysis step.

45. A process according to claim 28, wherein no further separation steps regarding the aqueous mixture are needed after the acid hydrolysis step.

46. A process according to claim 32, wherein the aqueous mixture further comprises formic acid.

47. A process according to claim 46, wherein the aqueous mixture further comprises furfural.

48. A process according to claim 32, wherein no further concentration steps regarding the aqueous mixture are needed after the acid hydrolysis step.

49. A process according to claim 32, wherein no further separation steps regarding the aqueous mixture are needed after the acid hydrolysis step.

* * * * *

UNITED STATES PATENT AND TRADEMARK OFFICE
CERTIFICATE OF CORRECTION

| | | |
|---|---|---|
| PATENT NO. | : 7,378,549 B2 | Page 1 of 1 |
| APPLICATION NO. | : 11/041324 | |
| DATED | : May 27, 2008 | |
| INVENTOR(S) | : Paul Marie Ayoub | |

It is certified that error appears in the above-identified patent and that said Letters Patent is hereby corrected as shown below:

Title Pg, Item (54) Title, please delete "EXTRACTIVE"

In Claim 17, please replace "60 to 150° C" with "80 to 120° C"

Signed and Sealed this

Twenty-sixth Day of May, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,378,549 B2 Page 1 of 1
APPLICATION NO. : 11/041324
DATED : May 27, 2008
INVENTOR(S) : Paul Marie Ayoub It is certified that error appears in the above-identified patent and that said Letters Patent is hereby corrected as shown below:

Title Pg, Item (54) and Column 1, line 2 Title, please delete "EXTRACTIVE"

Column 10, in Claim 17, line 21, please replace "60 to 150° C" with "80 to 120° C"

This certificate supersedes the Certificate of Correction issued May 26, 2009.

Signed and Sealed this

Sixteenth Day of June, 2009

JOHN DOLL
*Acting Director of the United States Patent and Trademark Office*